United States Patent
Iwakiri et al.

(10) Patent No.: US 9,127,099 B2
(45) Date of Patent: Sep. 8, 2015

(54) POLYMER AND METHOD FOR PRODUCING SAME

(75) Inventors: Norio Iwakiri, Tsukuba (JP); Yosuke Matsuoka, Tsukuba (JP); Nobuyuki Yoshioka, Tsukuba (JP); Yuki Yamashita, Tsukuba (JP); Nobuyuki Sakamoto, Tsukuba (JP)

(73) Assignee: NOF CORPORATION, Tokyo (JP)

( * ) Notice: Subject to any disclaimer, the term of this patent is extended or adjusted under 35 U.S.C. 154(b) by 56 days.

(21) Appl. No.: 14/129,490

(22) PCT Filed: Jun. 12, 2012

(86) PCT No.: PCT/JP2012/065040
§ 371 (c)(1),
(2), (4) Date: Dec. 26, 2013

(87) PCT Pub. No.: WO2013/002021
PCT Pub. Date: Jan. 3, 2013

(65) Prior Publication Data
US 2014/0142240 A1 May 22, 2014

(30) Foreign Application Priority Data
Jun. 27, 2011 (JP) .................... 2011-142253

(51) Int. Cl.
| C08F 130/02 | (2006.01) |
| A61L 27/34 | (2006.01) |
| A61L 29/08 | (2006.01) |
| A61L 31/10 | (2006.01) |
| C08F 230/02 | (2006.01) |
| C08F 220/32 | (2006.01) |

(52) U.S. Cl.
CPC .............. *C08F 130/02* (2013.01); *A61L 27/34* (2013.01); *A61L 29/085* (2013.01); *A61L 31/10* (2013.01); *C08F 230/02* (2013.01); *C08F 220/32* (2013.01)

(58) Field of Classification Search
CPC ....... A61L 27/34; A61L 29/085; A61L 31/10; C08F 130/02; C08F 230/02; C08F 220/32
USPC ..................... 526/274; 524/547; 525/326.6
See application file for complete search history.

(56) References Cited

U.S. PATENT DOCUMENTS

| 5,556,710 A | 9/1996 | Russell et al. |
| 6,090,901 A | 7/2000 | Bowers et al. |
| 6,440,565 B1 | 8/2002 | Kim et al. |
| 6,653,423 B1 | 11/2003 | Yamamoto et al. |
| 2006/0252148 A1 * | 11/2006 | Kurosawa et al. ............ 435/366 |
| 2010/0028399 A1 | 2/2010 | Hornof |
| 2013/0310591 A1 | 11/2013 | Yoshioka et al. |

FOREIGN PATENT DOCUMENTS

| EP | 0861858 A2 | 9/1998 |
| EP | 1211268 A1 | 6/2002 |
| EP | 2107913 B1 | 2/2012 |
| EP | 2669287 A1 | 12/2013 |
| JP | 05-300940 A | 11/1993 |
| JP | 6-88381 A | 3/1994 |
| JP | 07184990 A | 7/1995 |
| JP | 10-152533 A | 6/1998 |
| JP | 2002-030117 A | 1/2002 |
| JP | 2002-348779 A | 12/2002 |
| JP | 2007-155387 A | 6/2007 |
| JP | 2010-059367 A | 3/2010 |
| WO | 01/05855 A1 | 1/2001 |
| WO | 2008023872 A1 | 2/2008 |

OTHER PUBLICATIONS

International Searching Authority, International Search Report of PCT/JP2012/065040 dated Jul. 31, 2012.
European Patent Office, Communication dated Oct. 7, 2014, issued in corresponding European application No. 12803914.6.
International Searching Authority, International Preliminary Report on Patentability dated Jan. 7, 2014, issued in counterpart International application No. PCT/JP2012/065040.

* cited by examiner

*Primary Examiner* — Ling Choi
*Assistant Examiner* — Chun-Cheng Wang
(74) *Attorney, Agent, or Firm* — Sughrue Mion, PLLC

(57) ABSTRACT

Provided are a polymer having low cytotoxicity and capable of imparting surface hydrophilicity and biocompatibility to medical device surfaces by simple processing, a method for producing the polymer, and a surface treatment agent for medical devices. The polymer of the present invention has a particular ratio of structural units represented by the formulae (1a) and (1b), and a particular weight average molecular weight, and is useful as a surface treatment agent for various medical devices.

3 Claims, 1 Drawing Sheet

POLYMER AND METHOD FOR PRODUCING SAME

CROSS REFERENCE TO RELATED APPLICATIONS

This is a National Stage of International Application No. PCT/JP2012/065040 filed Jun. 12, 2012, claiming priority based on Japanese Patent Application No. 2011-142253 filed Jun. 27, 2011, the contents of all of which are incorporated herein by reference in their entirety.

FIELD OF ART

The present invention relates to a novel polymer that is useful for imparting biocompatibility to medical devices which come into contact with living tissues, a method for producing the same, and a surface treatment agent for medical devices utilizing the polymer.

BACKGROUND ART

There are conventionally known techniques of imparting lubricity to medical device surfaces by coating (e.g., Patent Publication 1). Patent Publication 2 proposes use of a copolymer of 2-methacryloyloxyethyl-2-trimethylammonioethyl phosphate (abbreviated as MPC hereinbelow) and allylamine (abbreviated as AAM hereinbelow) on medical device surfaces for improved biocompatibility.

However, AAM is highly toxic and inconvenient in handling, so that it is not preferred to increase the compositional ratio of AAM in the copolymer.

Patent Publication 3 proposes reacting MPC copolymer having primary amino groups, which is obtained by copolymerization of MPC and 2-aminoethylmethacrylate (abbreviated as AEMA hereinbelow), with reactive surfaces of medical devices. According to this method, the copolymer having highly reactive amino groups is chemically bonded to medical device surfaces, so that an increased amount of amino groups are introduced, resulting in highly durable surfaces.

However, cationic property of the functional groups remaining unreacted may cause protein adsorption, activation of immune cells, or adsorption to cells, which may deteriorate the biocompatibility.

Patent Publication 1: JP-H05-300940-A
Patent Publication 2: WO 2001/05855
Patent Publication 3: US-6090901

SUMMARY OF THE INVENTION

It is an object of the present invention to provide a polymer having low cytotoxicity and capable of imparting surface hydrophilicity and biocompatibility to medical device surfaces by simple processing, and a method for producing the polymer.

It is another object of the present invention to provide a surface treatment agent for medical devices, having low cytotoxicity and capable of imparting surface hydrophilicity and biocompatibility to medical device surfaces by simple processing.

The present inventors have made intensive researches in the light of the above objects to find out that reaction of a particular polymer having a phosphorylcholine-like group with 2-aminoethanethiol yields a polymer that is capable of improving surface hydrophilicity of medical devices, and has high biocompatibility and low cytotoxicity even when its reactivity to surfaces is low, to thereby complete the present invention.

According to the present invention, there is provided a polymer comprising structural units represented by the formulae (1a) and (1b), and having a weight average molecular weight of 10000 to 5000000:

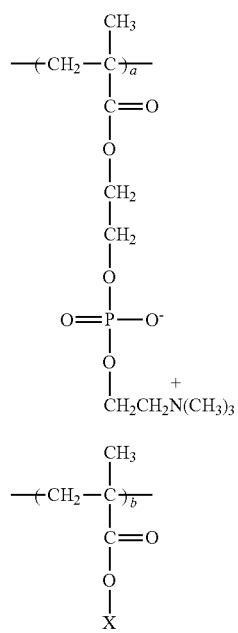

Formula (1a)

Formula (1b)

wherein X stands for a group represented by the formula:

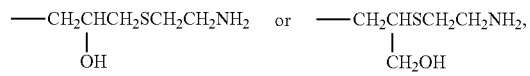

and a and b satisfy $(b/(a+b)) \times 100 = 5$ to 30.

According to the present invention, there is also provided a method for producing this polymer comprising polymerization of a monomer composition comprising MPC presented by the formula (2a) and glycidyl methacrylate represented by the formula (2b) (abbreviated as GMA hereinbelow) at a molar ratio of GMA being 5 to 30% of a total amount of MPC and GMA, followed by reaction with 2-aminoethanethiol represented by the formula (3) (abbreviated as AET hereinbelow):

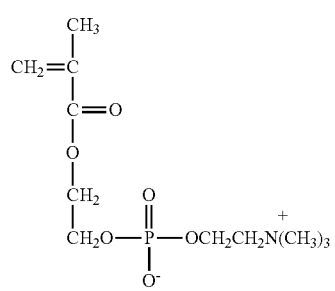

Formula (2a)

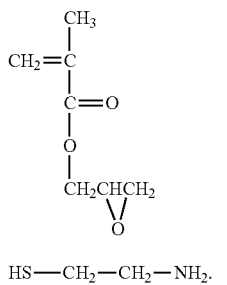

Formula (2b)

HS—CH₂—CH₂—NH₂.   Formula (3)

According to the present invention, there is further provided a surface treatment agent for a medical device consisting of an aqueous solution comprising 0.1 to 20 mass % of the polymer.

The polymer according to the present invention, having the structure mentioned above, capable of imparting hydrophilicity and biocompatibility to medical device surfaces by simple processing, and having low cytotoxicity, is useful as a surface treatment agent for medical devices which come into contact with body fluid or blood, such as guidewires, catheters, artificial vessels, cardiopulmonary bypasses, contact lenses, and intraocular lenses.

PREFERRED EMBODIMENTS OF THE INVENTION

Figure 1:
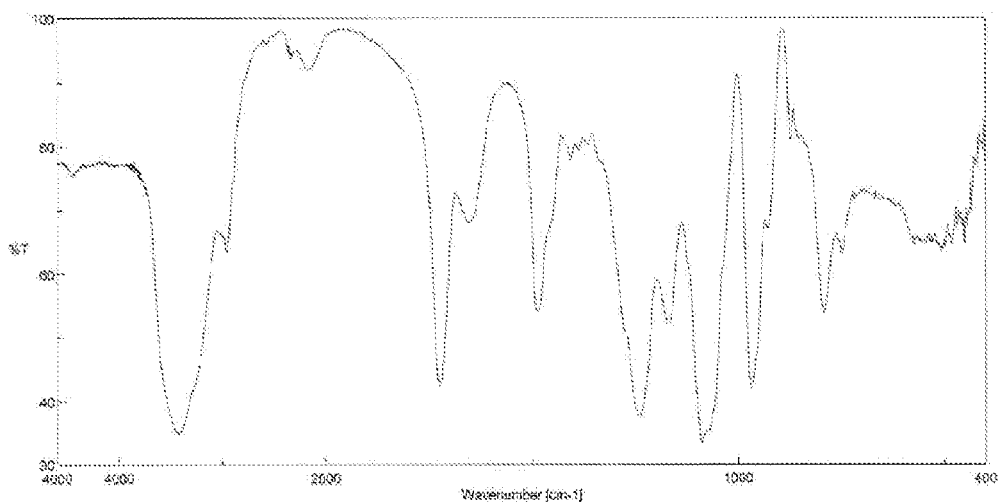
FIG. 1 is the IR spectrum of the polymer prepared in Example 1.

The present invention will now be explained in detail.

The polymer according to the present invention has structural units represented by the formulae (1a) and (1b) above and a weight average molecular weight of 10000 to 5000000, preferably 100000 to 1500000, and may optionally have a structural unit or units other than those represented by the formulae (1a) and (1b). With a weight average molecular weight of less than 10000, adhesivity to medical device surfaces is not sufficient, which may cause inferior durability, whereas with a weight average molecular weight of over 5000000, viscosity of the polymer during its production is too high, which may cause difficulties in handling.

In the formulae (1a) and (1b), X stands for a group represented by the formula:

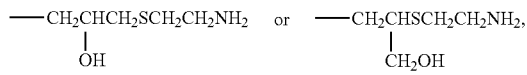

and a and b each represent a molar ratio of each structural unit and satisfy $(b/(a+b))\times 100=5$ to 30. When $(b/(a+b))\times 100$ is less than 5, adhesivity to medical device surfaces is not sufficient, durability may be low, and surface hydrophilicity may not be improved. When $(b/(a+b))\times 100$ is over 30, cytotoxicity may be high.

The polymer of the present invention may be obtained, for example, by the method of the present invention wherein a monomer composition containing MPC represented by the formula (2a) and GMA represented by the formula (2b) at the molar ratio of GMA being 5 to 30% of the total amount of MPC and GMA, is polymerized, and then reacted with AET represented by the formula (3).

The polymerization of the monomer composition may be carried out, for example, in the presence of a radical polymerization initiator in an atmosphere of or substituted with an inert gas, such as nitrogen, carbon dioxide, argon, or helium, by a known method, for example radical polymerization, such as bulk, suspension, emulsion, or solution polymerization. In view of purification or the like of the resulting polymer, solution polymerization is preferred. Through this polymerization, a polymer having a structural unit represented by the formula (2) is obtained:

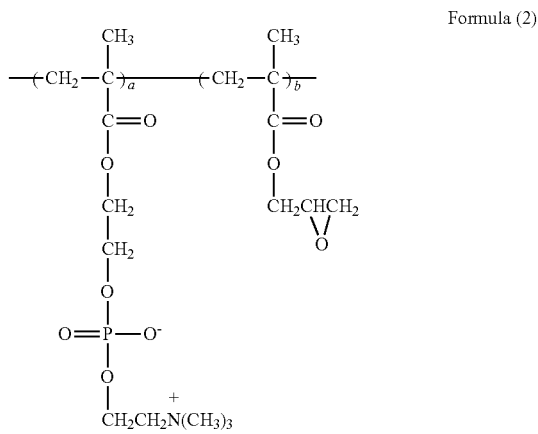

Formula (2)

wherein a and b may either be random or block, and satisfy $(b/(a+b))\times 100=5$ to 30. Purification of the polymer may be carried out by a common method, such as reprecipitation, dialysis, or ultrafiltration.

The radical polymerization initiator may be an azo radical polymerization initiator, such as 2,2-azobis(2-amidinopropyl)dihydrochloride, 2,2-azobis(2-(5-methyl-2-imidazoline-2-il)propane)dihydrochloride, 4,4-azobis(4-cyanovaleric acid), 2,2-azobisisobutylamide dihydrate, 2,2-azobis(2,4-dimethylvaleronitrile), 2,2-azobisisobutylonitrile (AIBN), dimethyl-2,2'-azobisisobutylate, 1-(1-cyano-1-methylethyl) azo)formamide, 2,2'-azobis(2-methyl-N-phenylpropionamidine)dihydrochloride, 2,2'-azobis(2-methyl-N-(2-hydroxyethyl)-propionamide, 2,2'-azobis(2-methylpropionamide) dehydrate, 4,4'-azobis(4-cyanopentanoic acid), or 2,2'-azobis (2-(hydroxymethyl)propionitrile). Further, organic peroxides may also be used, such as benzoyl peroxide, diisopropyl peroxydicarbonate, t-butylperoxy-2-ethylhexanoate, t-butyl peroxypivalate, t-butyl peroxydiisobutyrate, lauroyl peroxide, t-butyl peroxyneodecanoate, succinylperoxide, glutarperoxide, succinyl peroxyglutarate, t-butyl peroxymaleate, t-butyl peroxypivalate, di-2-ethoxyethyl peroxycarbonate, or 3-hydroxy-1,1-dimethylbutyl peroxypivalate. Further, persulfates may also be used, such as ammonium persulfate, potassium persulfate, or sodium persulfate. One or a mixture of these radical polymerization initiators may be used. The amount of the polymerization initiator is usually 0.001 to 10 parts by mass, preferably 0.01 to 5.0 parts by mass with respect to 100 parts by mass of the monomer composition.

The polymerization of the monomer composition may be carried out in the presence of a solvent. The solvent may be selected from those which dissolve the monomer composition without reacting therewith, for example, water; alcohol solvents, such as methanol, ethanol, n-propanol, or isopropanol; ketone solvents, such as acetone, methyl ethyl ketone, or diethyl ketone; ester solvents, such as ethyl acetate; straight or cyclic ether solvents, such as ethyl cellosolve, tetrahydrofuran, or N-methylpyrrolidone; or nitrogen-containing solvents, such as acetonitrile, or nitromethane. Preferred is water, alcohol, or a mixed solvent thereof.

The resulting polymer represented by the formula (2) may be used in the next reaction after purification or dilution of the polymerization solvent without further processing.

The reaction of the polymer represented by the formula (2), which is obtained through polymerization of the monomer composition, with AET represented by the formula (3) may be carried out in a solvent under heating. The resulting polymer may be purified by a common process, such as reprecipitation, dialysis, or ultrafiltration.

The solvent may be selected from those which dissolve the polymer of the formula (2) and AET without reacting therewith, for example, protic solvents, such as methanol, ethanol, n-propanol, or isopropanol, with n-propanol being preferred for its reactivity.

The solution concentration of the polymer of the formula (2) upon reaction is preferably 4 to 30 mass %. At over 30 mass %, viscosity of the reaction solution is high and the reaction may not proceed sufficiently. At less than 4 mass %, the amount of the reaction solvent is large and the production efficiency may be low.

The amounts of the polymer of the formula (2) and AET are preferably such that the molar ratio of the epoxy groups in the polymer of the formula (2) to AET is 1:3 to 100. The molar ratio of AET over 100 is not economical, whereas the molar ratio of AET less than 3 may cause side reaction, and the desired water-soluble polymer may not result.

The reaction hitherto discussed may be carried out either by adding AET to the polymer of the formula (2) or by adding the polymer of the formula (2) to AET. In the case of the former, AET may be dissolved in the solvent prior to the addition, or may be added as it is. However, gradual addition of AET may cause side reaction, and the desired water-soluble polymer may not result, and thus addition in a lump is preferred.

The reaction temperature is preferably 40 to 100° C. At less than 40° C., the reaction may not proceed sufficiently, whereas at over 100° C., the resulting polymer may decompose.

The reaction time is preferably not less than 3 hours and not more than 48 hours. With less than 3 hours, control of the reaction may be hard, whereas with over 48 hours, side reaction may occur, resulting in low purity of the obtained polymer.

It is preferred to carry out the reaction with the atmosphere of the reaction vessel substituted with an inert gas, such as nitrogen or argon, so that the thiol group in AET is prevented from being oxidized into disulfide.

When the reaction is completed, the obtained reaction liquid may be purified by a common process, such as reprecipitation, dialysis, or ultrafiltration, to obtain the objective polymer.

The surface treatment agent for medical devices according to the present invention is composed of an aqueous solution containing 0.1 to 20 mass % of the polymer of the present invention. At the polymer content of the aqueous solution of less than 0.1 mass %, reactivity with the medical device surface is low, whereas at over 20 mass %, the viscosity of the aqueous solution is too high, which may cause difficulties in handling.

The surface treatment agent for medical devices according to the present invention may be used, for example, by application to a medical device surface or by immersion of a medical device in the surface treatment agent for medical devices, to thereby fix the polymer of the present invention.

The fixing may be effected, for example, by covalent bonding, ion bonding, or coordinate bonding the polymer of the present invention to a medical device surface. In view of durability, covalent bonding is preferred.

A covalent bond may be established, for example, by causing a functional group which is reactive to the amino group in the present polymer, to be present on a medical device surface, and covalently bonding these groups.

The functional group may be, for example, a carboxyl, carboxylic acid anhydride, epoxy, or isocyanate group. When only the functional groups unreactive to the amino group, such as an amino or hydroxyl group, are present on a medical device surface, the surface may be converted to have functional groups by means of a polyfunctional reagent, such as diisocyanate or diepoxy, to render the surface reactive to the amino group.

When a medical device is made of polyethylene or the like, which is totally free of functional groups, the surface of the medical device may be treated with plasma, corona, or ozone to provide the surface with, for example, carboxyl groups, to thereby render the surface reactive to the amino group.

The covalent bond may be established by suitably selecting the conditions from conventional ones, depending on the kind and amount of the functional group, the material from which the medical device is made, or the like.

The medical device to which the surface treatment agent of the present invention is applied, may be those which come into contact with body fluid or blood, such as guidewires, catheters, artificial vessels, cardiopulmonary bypass, contact lenses, and intraocular lenses.

EXAMPLES

The present invention will now be explained in more detail with reference to Examples, which do not limit the present invention. Various measurements in the following Examples were made as described below.

<Quantification of Amino Groups in Compound>

Quantification of amino groups was performed with 2,4,6-trinitrobenzene sodium sulfonate (abbreviated as TNBS hereinbelow). Specifically, 0.01 g of the obtained polymer was dissolved in 9.99 g of distilled water, to which 4 mL of a 113 mM borate buffer, 1 mL of a 11.4 mM $Na_2SO_3$ aqueous solution, and 1 mL of 3.8 mM TNBS were added, and reacted at 37° C. for 1 hour. When the reaction was completed, the absorbance at a wavelength of 420 nm was determined with an ultraviolet-visible spectrophotometer (V-550, manufactured by JASCO CORPORATION), and the ratio of amino groups introduced into the polymer was calculated.

<Measurement of Weight Average Molecular Weight>

The measurement was made of 5 mg of the obtained polymer dissolved in 1 g of a 0.1 mol/L sodium nitrate aqueous solution. The remaining conditions for the measurement were as follows:

column: Shodex (GSM-700); eluting solvent: 0.1 mol/L sodium nitrate aqueous solution; reference material: pullulan; detection: differential refractometer RI-8020 (manufactured by TOSOH CORPORATION); calculation of weight average molecular weight (Mw): molecular weight calculation program (GPC program for S-8020); flow rate: 1.0 ml/min; column temperature: 40° C.; sample injection volume: 100 μL; measurement time: 30 min.

<Cytotoxicity Test>

Cytotoxicity was tested with reference to ISO10993-5: 2009 and N. Tani et al., Toxicology in vitro 13(1999), 175-187, and evaluated based on the cell survival rate.

Preparation of Cell Culture Medium

To a 500 mL bottle of a Dulbecco's modification of Eagle's medium (DMEM), 5 mL of an antibiotic/antifungal solution (100×) was introduced through a polyvinylidene fluoride (PVDF) sterilizing filter (0.22 µm). Then, 50 mL of sterilized fetal bovine serum (FBS) was thawed at 4° C. and added to the bottle to prepare a cell culture medium.

Cell Culture

In a sterile petri dish, 9 mL of the cell culture medium and 1 mL of a cell suspension were placed, and cultured in a $CO_2$ incubator for over 48 hours to proliferate the cells. The cells in the petri dish were microscopically observed to confirm cell count increase and the state of the cells (whether the cells were not killed or floating without being adhered).

Cell Seeding

The cell suspension was adjusted to the concentration of $1 \times 10^5$ cells/mL with the cell culture medium. The adjusted cell suspension was dispensed into a 96-well plate at 100 µL/well with a micropipette, and incubated for 24 hours in a $CO_2$ incubator.

Preparation of Polymer Solution

The polymer sample and sodium lauryl sulfate (SLS) of biochemical grade as a positive control were each dissolved in the cell culture medium and Dulbecco's phosphate-buffered saline (PBS) (10×), and sterilized through a PVDF sterilizing filter (0.22 µm). The polymer solution thus prepared (test sample) was serially diluted on a 96-well plate.

Exposure to Test Sample

The test sample of 1.0 mass % polymer content prepared above was added at 100 µL/well to the 24-hour-incubated 96-well plate for exposure in a $CO_2$ incubator for 24 hours.

Cytotoxicity Assay by Neutral Red (NR)

NR was dissolved in ion-exchanged water at 5 mg/mL to prepare a NR stock solution. The NR stock solution was diluted by 100 folds with the cell culture medium to prepare a NR medium. The 96-well plate exposed to the test sample was taken out, the medium was discharged into a basin, and the plate was patted on Kimtowel to remove the residual medium. Then the NR medium was added to the 96-well plate at 100 µL/well with a micropipette, and incubated in a $CO_2$ incubator for 3 hours to allow the cells to take in NR.

The 96-well plate was taken out of the $CO_2$ incubator, and the NR medium was removed. PBS was added at 100 µL/well, and then removed. A NR extractant containing 50 mass % ethanol, 49 mass % ion exchanged water, and 1 mass % acetic acid was added at 100 µL/well with a micropipette, and shaken with a shaking apparatus for five minutes to extract NR from the cells. The absorption at 540 nm was determined with a plate reader.

According to the formula below, the SLS contact concentration at 50% cell survival rate was confirmed to be about 0.01 mass %, and the survival rate of the cells when treated with the test sample was calculated:

Cell survival rate=(Absorption when treated with test sample−Absorption of blank)/(Absorption when treated with medium−Absorption of blank)×100

Preparation of Methacrylic Acid (MAA)-Grafted Polyethylene (PE) Film

A 1×4 cm polyethylene film was placed between the electrodes of a corona discharge device with the electrode interval of 3 cm at a voltage across the electrodes of 15 kV to effect a discharge treatment. Then the film was immersed in a 10 mass % methacrylic acid aqueous solution, deaerated, and subjected to graft polymerization in vacuum. After the polymerization, the film was thoroughly washed with water, to obtain a MAA-grafted PE film.

Preparation of Polymer-Grafted Film

The 1×4 cm MAA-grafted PE film prepared above was immersed in 4.0 g of a 5 mass % aqueous solution of the polymer prepared in each Example or Comparative Example to be discussed later, also containing 0.04 g of water-soluble carbodiimide, to effect coupling reaction at room temperature for 24 hours. After this treatment, the film was washed with water, to thereby obtain a polymer-grafted film, which was subjected to the following evaluations.

XPS (X-Ray Photoelectron Spectroscopy) Evaluation

The film surface was analyzed by XPS, and the amount of the adhered polymer was calculated.

Evaluation criteria:
A: 90% or more of the theoretical
B: not less than 50% and less than 90% of the theoretical
C: less than 50% of the theoretical Surface Hydrophilicity Evaluation The polymer-grafted film, which had been immersed in water, was drawn out of the water, and the time lapsed before the water film was broken was measured to evaluate the surface hydrophilicity. The evaluation was made as follows:

Evaluation Criteria:
A: more than 30 seconds lapsed before the water film was broken.
B: more than 10 seconds and less than 30 seconds lapsed before the water film was broken.
C: less than 10 seconds lapsed before the water film was broken.

Evaluation of Protein Adsorption

Preparation of Phosphate Buffer 0.900 g of sodium chloride and 0.104 g of monobasic sodium phosphate were measured out and placed in a 100 cc measuring flask, to which ion exchanged water was added to make the total volume 100 mL. To this mixture, 1 N sodium hydroxide aqueous solution was added to adjust the pH to about 7.4, to thereby obtain a phosphate buffer.

Preparation of Soiling Protein Solution 0.388 g of albumin, 0.161 g of γ-globulin, 0.120 g of lysozyme, and 0.100 g of mucin were measured out, and 100 mL of the phosphate buffer was added to disperse. An aqueous solution of 1M potassium chloride was further added and uniformly mixed to give a soiling protein solution. Preparation of Extractant Liquid To a 100 cc measuring flask was introduced 50 mL of ion exchanged water and then 148 µL of trifluoroacetic acid, and the resulting mixture was diluted with ion exchanged water to 100 mL.

The solution thus prepared was mixed with 100 mL of acetonitrile to give an extractant liquid.

Protein Adsorption Test

Two 1×4 cm polymer-grafted films were immersed in 32 mL of the soiling protein solution, and left to stand at 37° C. for 4 hours. Then the films were rinsed with saline, and immersed in 32 mL of the extractant liquid to effect extraction for 1 hour. The liquid after the extraction was taken by 200 µL, diluted with 800 µL of the extractant liquid, 1 mL of Micro BCA reagent was added, and heated at 60° C. for 1 hour. The absorption of the resulting solution at 562 nm was measured to calculate the amount of the adsorbed protein.

Evaluation Criteria:
A: (protein adsorption of sample/protein adsorption of blank)<0.2

B: 0.2≤(protein adsorption of sample/protein adsorption of blank)<0.8

C: 0.8≤(protein adsorption of sample/protein adsorption of blank)

Here, a PE film was used as the blank.

Example 1-1

Figure 2:
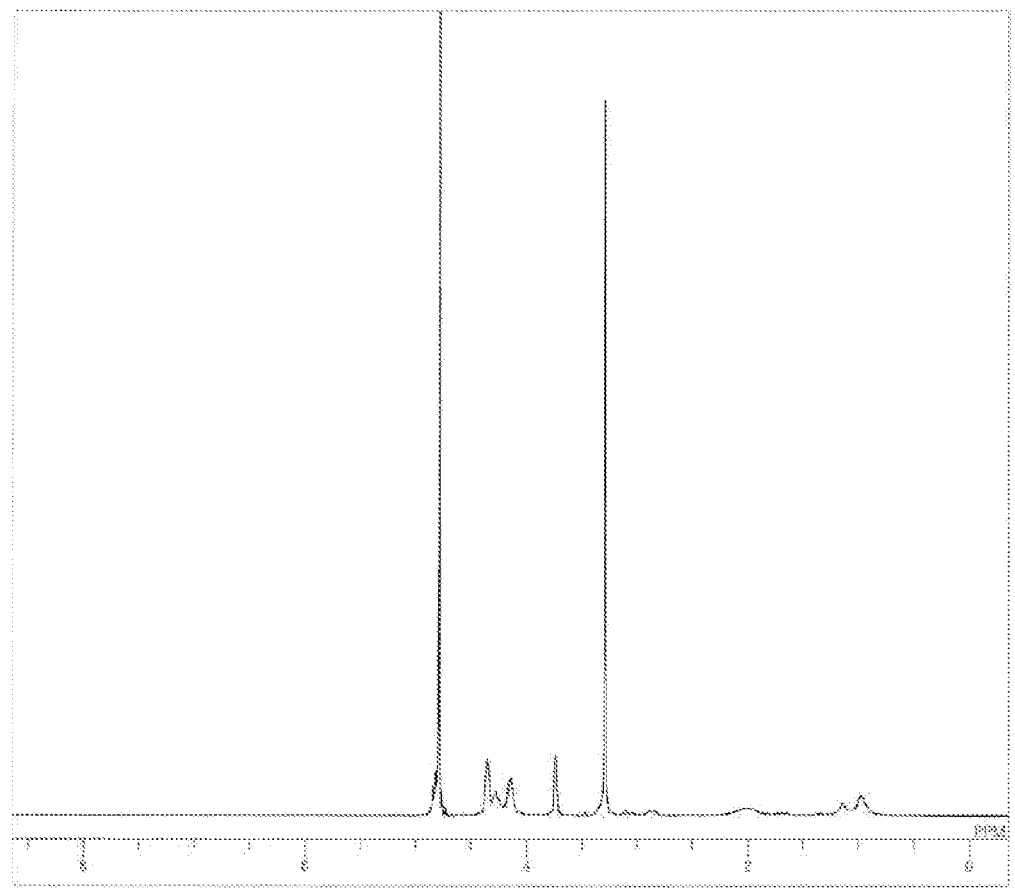
FIG. 2 is the $^1$H NHR spectrum of the polymer prepared in Example 1.

68.3 g of MPC (manufactured by NOF CORPORATION) and 1.7 g of GMA (manufactured by NOF CORPORATION) were dissolved in 210.0 g of n-propanol (NPA, manufactured by KISHIDA CHEMICAL CO., LTD.), placed in a 500 mL four-neck flask equipped with a thermometer and a cooling tube, and blown with nitrogen for 30 minutes. Then 0.27 g of t-butyl peroxyneodecanoate (PB-ND, manufactured by NOF CORPORATION) was added at 60° C., and polymerized for 8 hours. The chemical structure of the obtained polymer was confirmed by IR and $^1$H NMR. Next, to 280.0 g of this polymer solution (solution of the polymer represented by formula (2)) was added 157.5 g of NPA, and mixed into a uniform mixture. In this mixture, 9.8 g of AET (manufactured by WAKO PURE CHEMICAL INDUSTRIES, LTD.) was dissolved, heated, and stirred at 74° C. for 12 hours. When the reaction was completed, the resulting mixture was subjected to dialytic purification and freeze drying to recover white powdery polymer. The obtained polymer was subjected to IR, $^1$H NMR, elemental analysis, amino group quantification, and measurement of weight average molecular weight. The results are shown below and in Table 1. The IR and $^1$H NMR spectra are shown in FIGS. 1 and 2, respectively.

IR: 3425 cm$^{-1}$ (—OH), 2961 cm$^{-1}$ (—CH), 1724 cm$^{-1}$ (C=O), 1489 cm$^{-1}$ (—CH), 1241 cm$^{-1}$ (P=O), 1170 cm$^{-1}$ (C—O—C), 1089 cm$^{-1}$ (P—O—C), 968 cm$^{-1}$ (C—O—C).

$^1$H NMR data: 0.7-1.2 ppm (CH$_3$C—), 1.4-2.3 ppm (—CH$_2$C—), 2.7-3.1 ppm (—CH$_2$CH(OH)CH$_2$—, —OCH$_2$CHCH$_2$OH—), 3.3 ppm (—N(CH$_3$)$_3$), 3.5-4.4 ppm (—CH$_2$CH$_2$O—).

Elemental Analysis

Actual measured values:

C, 44.86%; H, 7.56%; N, 4.85%

Theoretical values:

C, 44.97%; H, 7.47%; N, 4.83%

Amount of amino groups introduced:

(b/(a+b)×100): 5 mol %

The above results show that the polymer had a weight average molecular weight of 650000, and the ratio of the units derived from MPC of the formula (1a) was 95 mol %, and the ratio of the units derived from the amino group of the formula (1b) was 5 mol %.

Example 1-2

66.4 g of MPC, 3.6 g of GMA, and 163.3 g of NPA were placed in a 500 mL four-neck flask equipped with a thermometer and a cooling tube, and blown with nitrogen for 30 minutes. Then 0.23 g of PB-ND was added at 60° C., and polymerized for 8 hours. The chemical structure of the obtained polymer was confirmed by IR and $^1$H NMR. Next, to 233.3 g of this polymer solution (solution of the polymer represented by formula (2)) was added 204.2 g of NPA, and mixed into a uniform mixture. In this mixture, 19.6 g of AET was dissolved, heated, and stirred at 74° C. for 12 hours. When the reaction was completed, the resulting mixture was subjected to dialytic purification and freeze drying to recover white powdery polymer. The obtained polymer was subjected to the measurements in the same way as in Example 1-1. The results are shown below and in Table 1.

IR: 3425 cm$^{-1}$ (—OH), 2961 cm$^{-1}$ (—CH), 1724 cm$^{-1}$ (C=O), 1489 cm$^{-1}$ (—CH), 1241 cm$^{-1}$ (P=O), 1170 cm$^{-1}$ (C—O—C), 1089 cm$^{-1}$ (P—O—C), 968 cm$^{-1}$ (C—O—C).

$^1$H NMR data: 0.7-1.2 ppm (CH$_3$C—), 1.4-2.3 ppm (—CH$_2$C—), 2.7-3.1 ppm (—CH$_2$CH(OH)CH$_2$—, —OCH$_2$CHCH$_2$OH—), 3.3 ppm (—N(CH$_3$)$_3$), 3.5-4.4 ppm (—CH$_2$CH$_2$O—).

Elemental Analysis

Actual measured values:

C, 45.11%; H, 7.63%; N, 4.86%

Theoretical values:

C, 45.20%; H, 7.49%; N, 4.91%

Amount of amino groups introduced:

(b/(a+b)×100): 10 mol %

The above results show that the polymer had a weight average molecular weight of 880000, and the ratio of the units derived from MPC of the formula (1a) was 90 mol %, and the ratio of the units derived from the amino group of the formula (1b) was 10 mol %.

Example 1-3

62.5 g of MPC, 7.5 g of GMA, and 210.0 g of NPA were placed in a 500 mL four-neck flask equipped with a thermometer and a cooing tube, and blown with nitrogen for 30 minutes. Then 0.27 g of PB-ND was added at 60° C., and polymerized for 8 hours. The chemical structure of the obtained polymer was confirmed by IR and $^1$H NMR. Next, to 280.0 g of this polymer solution (solution of the polymer represented by formula (2)) was added 157.5 g of NPA, and mixed into a uniform mixture. In this mixture, 39.3 g of AFT was dissolved, heated, and stirred at 74° C. for 12 hours. When the reaction was completed, the resulting mixture was subjected to dialytic purification and freeze drying to recover white powdery polymer. The obtained polymer was subjected to the measurements in the same way as in Example 1-1. The results are shown below and in Table 1.

IR: 3425 cm$^{-1}$ (—OH), 2961 cm$^{-1}$ (—CH), 1724 cm$^{-1}$ (C=O), 1489 cm$^{-1}$ (—CH), 1241 cm$^{-1}$ (P=O), 1170 cm$^{-1}$ (C—O—C), 1089 cm$^{-1}$ (P—O—C), 968 cm$^{-1}$ (C—O—C).

$^1$H NMR data: 0.7-1.2 ppm (CH$_3$C—), 1.4-2.3 ppm (—CH$_2$C—), 2.7-3.1 ppm (—CH$_2$CH(OH)CH$_2$—, —OCH$_2$CHCH$_2$OH—), 3.3 ppm (—N(CH$_3$)$_3$), 3.5-4.4 ppm (—CH$_2$CH$_2$O—).

Elemental Analysis

Actual measured values:

C, 45.47%; H, 7.69%; N, 5.10%

Theoretical values:

C, 45.66%; H, 7.52%; N, 5.08%

Amount of amino groups introduced:

(b/(a+b)×100): 20 mol %

The above results show that the polymer had a weight average molecular weight of 630000, and the ratio of the units derived from MPC of the formula (1a) was 80 mol %, and the ratio of the units derived from the amino group of the formula (1b) was 20 mol %.

Example 1-4

58.0 g of MPC, 12.0 g of GMA, and 163.3 g of NPA were placed in a 500 mL four-neck flask equipped with a thermometer and a cooling tube, and blown with nitrogen for 30 minutes. Then 0.23 g of PB-ND was added at 60° C., and polymerized for 8 hours. The chemical structure of the obtained polymer was confirmed by IR and $^1$H NMR. Next, to 233.3 g of this polymer solution (solution of the polymer represented by formula (2)) was added 204.2 g of NPA, and mixed into a uniform mixture. In this mixture, 58.9 g of AET was dissolved, heated, and stirred at 74° C. for 12 hours. When the reaction was completed, the resulting mixture was subjected to dialytic purification and freeze drying to recover white powdery polymer. The obtained polymer was subjected to the measurements in the same way as in Example 1-1. The results are shown below and in Table 1.

IR: 3425 cm$^{-1}$ (—OH), 2961 cm$^{-1}$ (—CH), 1724 cm$^{-1}$ (C=O), 1489 cm$^{-1}$ (—CH), 1241 cm$^{-1}$ (P=O), 1170 cm$^{-1}$ (C—O—C), 1089 cm$^{-1}$ (P—O—C), 968 cm$^{-1}$ (C—O—C).

$^1$H NMR data: 0.7-1.2 ppm (CH$_3$C—), 1.4-2.3 ppm (—CH$_2$C—), 2.7-3.1 ppm (—CH$_2$CH(OH)CH$_2$—, —OCH$_2$CHCH$_2$OH—), 3.3 ppm (—N(CH$_3$)$_3$), 3.5-4.4 ppm (—CH$_2$CH$_2$O—).

Elemental Analysis:
Actual measured values:
C, 45.47%; H, 7.69%; N, 5.10%
Theoretical values:
C, 45.66%; H, 7.52%; N, 5.08%
Amount of amino groups introduced:
(b/(a+b)×100): 30 mol %

Comparative Examples 1-1 and 1-2

The reactions in Example 1-1 were followed, except that the monomers, the solvent, and the initiator were replaced with those shown in Table 1. The obtained polymer was subjected to the measurements in the same way as in Example 1-1. The results are shown in Table 1.

Comparative Example 1-3

18.8 g of MPC and 1.2 g of AEMA (manufactured by ALDRICH) were dissolved in 80.0 g of ion exchanged water, placed in a 200 mL four-neck flask equipped with a thermometer and a cooling tube, and blown with nitrogen for 30 minutes. Then 0.1492 g of 2,2'-azobis(2-methylpropionamidine)dihydrochloride (V-50, manufactured by WAKO PURE CHEMICAL INDUSTRY, LTD.) was added at 60° C., and polymerized for 8 hours. The chemical structure of the obtained polymer was confirmed by IR and $^1$H NMR.

Comparative Examples 1-4 and 1-5

The polymerization in Comparative Example 1-3 was followed, except that the monomers, the solvent, and the initiator were replaced with those shown in Table 1. The chemical structure of the obtained polymer was confirmed by IR and $^1$H NMR.

TABLE 1

|  |  | Example | | | | Comparative Example | | | | |
|---|---|---|---|---|---|---|---|---|---|---|
|  |  | 1-1 | 1-2 | 1-3 | 1-4 | 1-1 | 1-2 | 1-3 | 1-4 | 1-5 |
| Starting material amount (g) | MPC | 68.3 | 66.4 | 62.5 | 58.0 | 69.7 | 53.0 | 18.8 | 17.7 | 20 |
|  | GMA | 1.7 | 3.6 | 7.5 | 12.0 | 0.3 | 17.0 | — | — | — |
|  | AEMA | — | — | — | — | — | — | 1.2 | 2.5 | — |
| Solvent (g) | NPA | 210.0 | 163.3 | 210.0 | 163.3 | 210.0 | 210.0 | — | — | — |
|  | Ion exchanged water | — | — | — | — | — | — | 80.0 | 80.0 | 80.0 |
| Initiator (g) | PB-ND | 0.27 | 0.23 | 0.27 | 0.23 | 0.27 | 0.27 | — | — | — |
|  | V-50 | — | — | — | — | — | — | 0.15 | 0.15 | 0.15 |
| GMA/MPC (in mole) |  | 5/95 | 10/90 | 20/80 | 30/70 | 1/99 | 40/60 | — | — | — |
| AEMA/MPC (in mole) |  | — | — | — | — | — | — | 10/90 | 20/80 | 0/100 |
| Starting material amount (g) | Polymer solution | 280.0 | 233.3 | 280.0 | 233.3 | 280.0 | 280.0 | — | — | — |
|  | NPA | 157.5 | 204.2 | 157.5 | 204.2 | 157.5 | 157.5 | — | — | — |
|  | AET (Formula (3)) | 9.8 | 19.6 | 39.3 | 58.9 | 2.0 | 78.5 | — | — | — |
| Formula (2b)/Formula (3) (in mole) |  | 1/10 | 1/10 | 1/10 | 1/10 | 1/10 | 1/10 | — | — | — |
| Reaction temperature |  | 74° C. | 74° C. | 74° C. | 74° C. | 74° C. | 74° C. | — | — | — |
| Reaction time |  | 12 hrs | 12 hrs | 12 hrs | 12 hrs | 12 hrs | 12 hrs | — | — | — |

The above results show that the polymer had a weight average molecular weight of 850000, and the ratio of the units derived from MPC of the formula (1a) was 70 mol %, and the ratio of the units derived from the amino group of the formula (1b) was 30 mol %.

The cytotoxicity test and the surface treatment tests were conducted on the polymers synthesized in Examples 1-1 to 1-4 and Comparative Examples 1-1 to 1-5 in accordance with the methods described above. The results are shown in Table 2.

TABLE 2

| | Sample used | | | | | | | | |
|---|---|---|---|---|---|---|---|---|---|
| | Example 1-1 | Example 1-2 | Example 1-3 | Example 1-4 | Comp. Ex. 1-1 | Comp. Ex. 1-2 | Comp. Ex. 1-3 | Comp. Ex. 1-4 | Comp. Ex. 1-5 |
| Amount of amino groups introduced | 5 | 10 | 20 | 30 | 1 | 40 | 10 | 20 | 0 |
| Weight average molecular weight | 650000 | 880000 | 610000 | 620000 | 640000 | 630000 | 800000 | 700000 | 720000 |
| Cell survival rate (%) | 108 | 106 | 99 | 98 | 109 | 52 | 35 | 7 | 99 |
| Result of surface treatment — XPS | A | A | A | A | C | A | A | A | C |
| Result of surface treatment — Surface hydrophilicity | A | A | A | A | C | A | A | A | C |
| Result of surface treatment — Protein adsorption | A | A | A | A | C | A | A | A | C |

The polymers of Examples 1-1 to 1-4 had higher cell survival rates than the polymers of Comparative Examples 1-2 to 1-4, and were demonstrated to be safe. Further, comparing the results of the surface treatment tests, the polymers of Examples 1-1 to 1-4 were demonstrated to have hydrophilic film surface and suppressed protein adsorption, compared to the polymers of Comparative Examples 1-1 and 1-5.

What is claimed is:

1. A polymer comprising structural units represented by the formulae (1a) and (1b), and having a weight average molecular weight of 10,000 to 5,000,000:

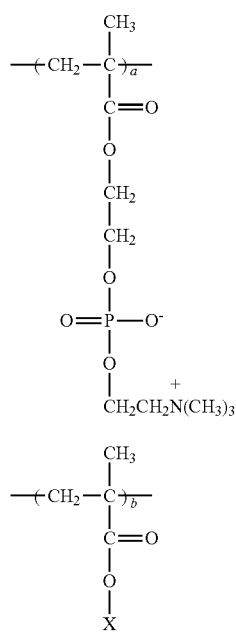

Formula (1a)

Formula (1b)

wherein X stands for a group represented by the formula:

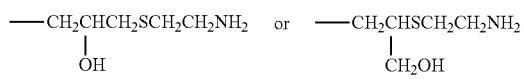

and a and b satisfy $(b/(a+b)) \times 100 = 5$ to $30$.

2. A method for producing the polymer of claim 1, comprising polymerization of 2-methacryloyloxyethyl-2-trimethylammonioethyl phosphate represented by the formula (2a) (MPC) and glycidyl methacrylate represented by the formula (2b) (GMA) at a molar ratio of GMA being 5 to 30% of a total amount of MPC and GMA, followed by reaction with 2-aminoethanethiol represented by the formula (3) (AET):

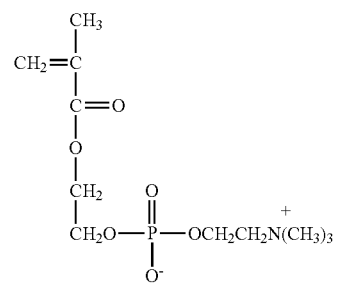

Formula (2a)

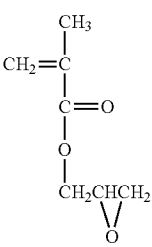

Formula (2b)

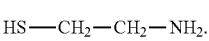

Formula (3)

3. A surface treatment agent for a medical device consisting of an aqueous solution comprising 0.1 to 20 mass % of the polymer of claim 1.

* * * * *